(12) United States Patent
Dutkiewicz

(10) Patent No.: US 6,257,236 B1
(45) Date of Patent: Jul. 10, 2001

(54) INTUBATION DEVICE

(76) Inventor: Edward P Dutkiewicz, 4205 Kent Dr., Largo, FL (US) 33774

( * ) Notice: Subject to any disclaimer, the term of this patent is extended or adjusted under 35 U.S.C. 154(b) by 0 days.

(21) Appl. No.: 09/256,440

(22) Filed: Feb. 23, 1999

(51) Int. Cl.[7] ................................................ A61M 16/00
(52) U.S. Cl. .............................. 128/207.14; 128/207.15; 128/206.29; 128/200.26
(58) Field of Search .................... 128/207.14, 207.15, 128/200.26, 200.11, 206.29, 206.21, 204.18, 204.21

(56) References Cited

U.S. PATENT DOCUMENTS

| | | | | |
|---|---|---|---|---|
| 4,727,872 | * | 3/1988 | Hawk ................. | 128/207.14 |
| 4,913,139 | * | 4/1990 | Ballew .............. | 128/200.11 |
| 4,960,122 | * | 10/1990 | Mizus ............... | 128/207.14 |
| 5,183,031 | * | 2/1993 | Rossoff .............. | 600/120 |
| 5,197,463 | * | 3/1993 | Jeshuran ........... | 128/207.14 |
| 5,277,175 | * | 1/1994 | Riggs et al. ...... | 128/200.21 |
| 5,607,386 | * | 3/1997 | Flam ................. | 600/120 |
| 5,694,929 | * | 12/1997 | Christopher ...... | 128/207.14 |

\* cited by examiner

*Primary Examiner*—Aaron J. Lewis
*Assistant Examiner*—V. Srivastava (57) ABSTRACT

This invention relates to a device for placement of an endotracheal tube, comprising a commonly used flexible fiberoptic Laryngoscope/Bronchoscope (FFLB), an anesthesia mask with a pluggable port, along with two hollow intubating stylettes, one short and one long, and a hook for retrieval of silk thread used in the intubating process with the shorter stylette. The anesthesia mask possesses a sealable port, with a distensible perforated membrane. The port is located over the mouth region of the mask, inferior to the gas circuit connecting inlet. The introducer/stylettes comprise a semi-rigid platic tubes. The shorter stylette/introducer has special thread holes, allowing the stylette to be secured with thread. The introducer allows an endotracheal tube to be slipped over it and into the patient's airway. The hook allows the rapid threading and advancing of the endotracheal tube over the shorter introducer/stylette. The use of the mask, stylette and hook combination allows the anesthesiologist or the nurse anesthetist to ventilate the patient and control the airway while using the fiberoptic laryngoscope to identify the larynx, and pass the intubating stylette into the trachea, rapidly followed with passage of an endotracheal tube, securing the airway.

2 Claims, 6 Drawing Sheets

INTUBATION DEVICE

BACKGROUND OF THE INVENTION

1. Field of the Invention

The present invention relates to a device, for the placement of an endotracheal tube into the trachea of the anesthetized patient, comprising a stylette/introducer which is placed into the trachea of said patient through a port in an anesthesia face mask, and then passing an endotracheal tube over the stylette, thereby securing the airway. The major advantage of this system is that the patient is ventilated during the most time consuming phase of the process, that is, the identification of the trachea and the passage of the stylette into it.

2. Prior Art

The necessity and advantage of endotracheal intubation in the application or anesthesia, and for pulmonary therapy is well documented and widely accepted. Intubation of the trachea was first accomplished in 1878 and since that time, the use of tracheal intubation in the patient with a difficult airway has been the anesthetist's most problematic situation.

Intubation of the trachea is necessary to protect a patient's airway during general anesthesia and to provide a way to ventilate the patient using positive pressure when the patient cannot adequately ventilate himself or herself. Intubation allows the use of positive pressure ventilation, continuous positive airway pressure, and positive end expiratory pressure.

Endotracheal intubation is now the standard of care in most operations, and its use now allows the introduction of carbon dioxide gas into the peritoneal cavity which facilitates the use of laporoscopic instrumentation to accomplish "band aid surgery" from within the peritoneal cavity rather than invasively, via large incisions, from the outside of the body.

The common practice during intubation is to cease ventilating the patient, insert the laryngoscope, visualize the opening of the trachea, and then, under direct vision, insert the endotracheal tube. After this is done, ventilation is re-instituted. In the instance of the difficult airway, where the tracheal opening cannot be visualized due to anomalies occurring in the structure of the airway, the practitioner may choose to utilize the fiberoptic laryngoscope to visualize the tracheal opening and to help insert the endotracheal tube. In order to accomplish this, the medical practitioner must cease ventilating the patient in order to use a fiberoptic laryngoscope to visualize the opening of the trachea. During this time the patient is not ventilated. The safety of the visualization of the tracheal opening in this manner, then, depends on the rapidity with which the practitioner can visualize the opening, and insert the endotracheal tube.

Various patents have been issued for devices which have attempted to deal with the problematic period of non-ventilation during the process of intubation. U.S. Pat. No. 5,197,463, SINGLE STAGE SEAL ADAPTOR FOR ENDOTRACHEAL INTUBATION AND REMOVAL ANESTHESIA MASK typifies these attempts to solve this problem. This consists of a "T" piece located on a specially designed mask which allows the take down of the top of the inlet to allow the passage of an endotracheal tube. U.S. Pat. No. 5,694,929 utilizes a guide which is an integral part of the anesthesia mask. The guide fits in the mask and enters the patient's mouth and, being a hollow tube, serves as a guide for the fiberoptic laryngoscope and endotracheal tube. While this device may allow the practitioner to intubate with the minimal disruption of ventilation, it appears that the connecting port of the ventilating endotracheal tube would have to be removed to fascilitate removal of the mask and airway from the tube which is placed through them. Care would have to be taken not to pull on the pilot tube of the endotracheal tube when this was being done. With the present invention, the only device in the patient's airway when the endotracheal tube is inserted, is the stylette/introducer, which pulls out of the airway from inside the endotracheal tube, once the airway is secure. This manipulation is simpler and more direct than other means necessary under the current art.

U.S. Pat. No. 5,623,921, known as the Laryngeal Mask Airway, is a device which, when placed within the patient's oropharynx, forms a seal around the opening of the trachea at the location of the superior larynx. The LMA, as it is widely known, does not completely seal the airway from aspirate. Another limitation is that only low pressures, less than 20 centimeters of water, can be used to ventilate the patient. This limitation prevents the usage in obese patients, or those surgical cases where greater pressures may be anticipated to be necessary.

Apparatus such as the Blachly BITE BLOCK ASSEMBLY, U.S. Pat. No. 4,112,936 and the Blachly OROPHARYNGEAL AIRWAY AND BITE BLOCK ASSEMBLY AND METHOD FOR CLOSED PULMONARY VENTILATION, U.S. Pat. No. 4,270,531 provide gas seal and the depth adjustability of the Northway-Meyer apparatus, but neither of the Blachly devices allows the placement of an endotracheal tube through the apparatus.

The ELAM MASK BREATHING SYSTEM U.S. Pat. No. 4,449,526 device does accommodate a fiberoptic laryngoscope and it does not accommodate an endotracheal tube. It's use is restricted to ventilation via the natural airway, such as in resuscitation.

BRIEF SUMMARY OF THE INVENTION

The present invention is a simple, practical device which utilizes four components; 1) a flexible fiberoptic laryngoscope/bronchoscope (FFLB); 2) an anesthesia mask with a special port located in the body of the mask; 3) one of two different sized introducer/stylettes; and 4) a thread retrieving device.

The fiberoptic laryngoscope may be any one of the number of currently available fiberoptic laryngoscopes or bronchoscopes, used in the medical field today.

The mask is in the configuration of a standard anesthesia mask commonly used currently in the practice, with the addition of the side port, located on either side of the circuit connecting port, over the position of the mouth. This pluggable port, with a distensible membrane, serves as an opening through which the FFLB may be introduced into the patient's airway, and into the trachea. The membrane of the port is a flexible dipharam-like cover, e.g. of a soft plastic material, such as silastic, having a skirt protion adapted to stretch over a lip of the main body of the port, and a cover portion with a central opening for receiving and allowing passage of the FLB/introducer assembly. The means of obturating the opening in the cover may comprise a slug of hard rubber or the like.

The introducer/stylettes are two. Both are tubes though which the FFLB is initially place before it is inserted into the port. Preferably the introducer/stylette, also referred to as the introducer, is a semi rigid plastic tube. The inside diameter of the introducer allows a slight clearance in the introducer around the FFLB. Preferably, the inside diameter of the introducer is about 1 to 1.5 mm larger than the diameter of the FFLB, approximately five to six millimeters. The reason there are two lenghts of stylettes is that there are various lengths of fiberoptic laryngoscopes. For the shorter fiberoptic laryngoscopes, the length of the introducer is sufficient to allow the introducer to be slid up to the proximal end of the FFLB so that its presence does not interfere with the practitioner as the FFLB is directed to, and placed within the trachea. Preferably the length of the introducer is about 35 cm. The distal end of the introducers are rounded and diagonally cut, having no sharp edges. The proximal end of the shorter introducer has two apertures through which a length of silk thread, preferable a silk thread about forty inches long, can be threaded. The proximal end of the longer introducer is plain, without apertures.

The hook is constructed of stiff wire, of suitable medical material. It has a small hook on the distal end enabling it to be advanced through the inside diameter of an endotracheal tube, and a larger loop on the proximal end, allowing the practitioner's finger to go through the loop to aid the practitioner in controlling the hook as he or she pulls the hook back through the endotracheal tube along with the thread. The small hook is not closed, allowing a thread to be pulled into its confines, while the larger loop can be closed.

An example of how these various components are used together to achieve the goal is as follows:

In order to fascilitate the process, and to shorten the time of apnea, the practitioner prepares the hook/endotracheal tube assembly before initiating the procedure in the following manner. The thread retrieval hook is placed through the endotracheal tube of choice, the hook end exiting the distal, cuffed end of the endotracheal tube. The hook/tube combination is handled as a unit.

The thread is placed through the introducer, and the introducer slipped over the FFLB. The tube and hook assembly is made ready, and placed at a convenient location, nearby. Then the FFLB is passed, via the mask port, into the oral cavity. Laryngoscopy is carried out, the opening to the trachea identified, and the FFLB passed into the trachea. Once this is done, the introducer is slipped over the tip of the FFLB, under direct visualization, and the FFLB is removed. The mask now has the introducer protruding from the port. At this point the practitioner holds the introducer in place and slips the mask off of the introducer. Next, the tube/hook unit is used. The hook, which protrudes from the distal end of the endotracheal tube is used to hook and capture the silk thread which is through the end of the introducer. Once the thread is securely on the hook, the hook is pulled through the endotracheal tube, bringing with it the thread, until the thread is completely through the endotracheal tube. The practitioner grasps the thread, which prevents the introducer from migrating downward as the tube is advanced over the introducer. Holding the thread firmly, the endotracheal tube is slipped over the introducer and into the airway. It is advanced downward, until it is advanced approximately 25 cm from the anterior tooth line, downward. Once the tube is fully advanced the introducer is removed and ventilation resumed after inflation of the cuff of the endotracheal tube. Breath sounds are auscultated and the endotracheal tube withdrawn until bilateral breath sounds are audible. If the practitioner has any question regarding position of the endotracheal tube, he or she may visually ascertain its position by advancing the FFLB down the endotracheal tube, and visually ascertaining the endotracheal tube's proper position.

The present device may also be used in conjunction with the Laryngeal Mask Airway, hereinafter, an LMA, in that the long sylette is slipped over a longer fiberoptic scope. The long scope is advanced down the LMA and into the trachea, at which point the scope is withdrawn, leaving the long stylette in place within the patient's trachea. This can be accomplished using a previously patented, commonly used, connector between the anesthesia circuit and the LMA. Once the stylette is in place and fiberoptic withdrawn, the end connector of an endotracheal tube can be placed on the stylette and ventilation checked by forcing gas down the hollow stylette into the patient's lungs. If ventilation is satisfactory the LMA can then be safely, carefully removed, leaving the stylette in place. Once the LMA is pulled off the stylette, the endotracheal tube can be advanced over it, and into position, in the patient's trachea.

The above description is exemplary, and not intended to limit the scope of the application of this invention.

DESCRIPTION OF THE PREFERRED EMBODIMENT

Referring now to the drawings by numbers of reference, a preferred intubating device which comprises the items described, that is, a mask, introducer/stylette, and hook, in accordance with the present invention, is designated the the numbers 14, 27, and 23 respectively.

Figures 1, 2:
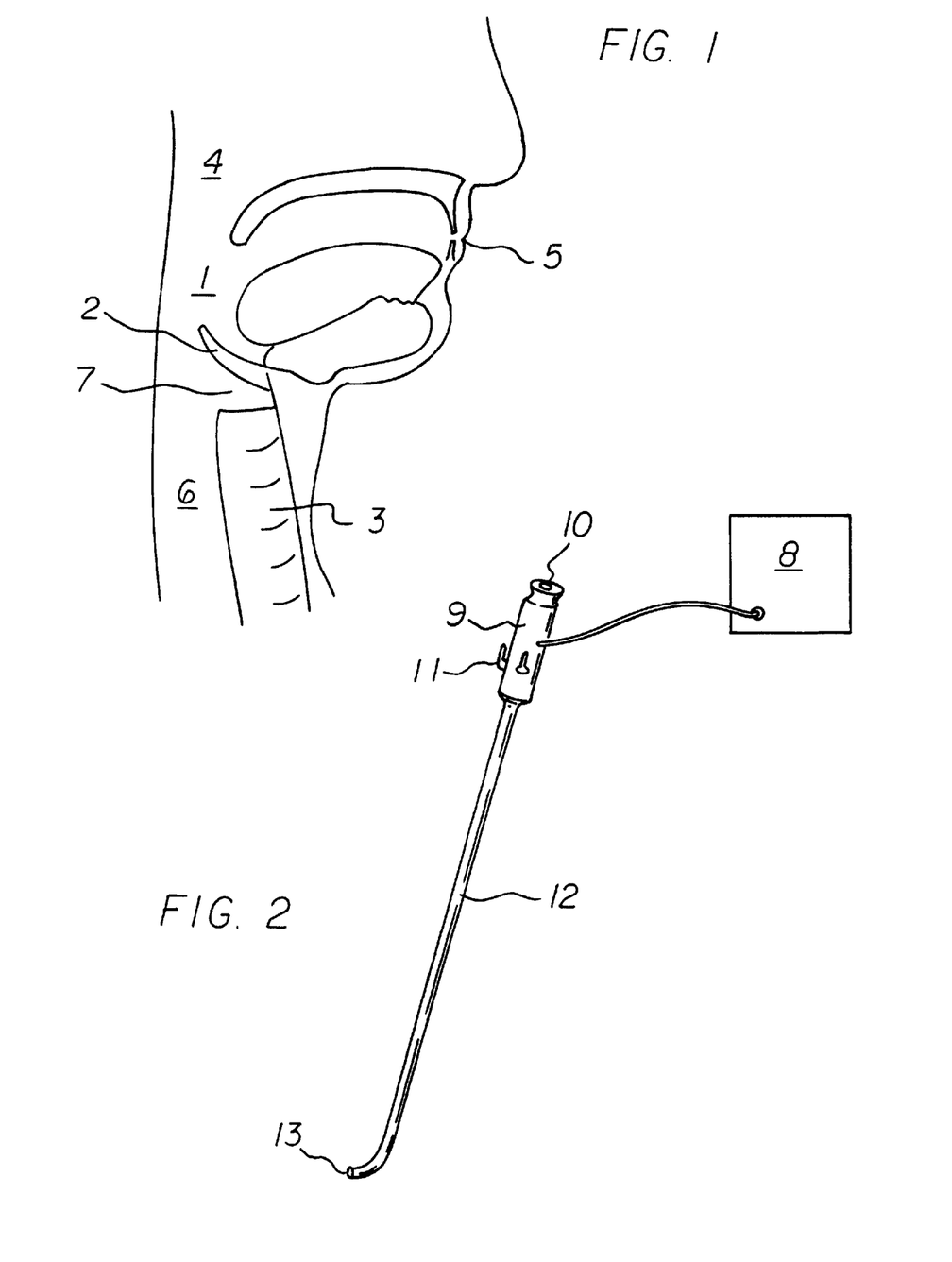
FIG. 1 is a cross section of the anatomy of the human airway.
FIG. 2 is a drawing of a fiberoptic scope 9 commonly used in the medical practice. The basic elements of such a scope are the light source 8, the eyepiece 10, the controls 11, the fiberoptic bundle 12 and the light emitting terminus and viewing apperture 13.

In FIG. 1. there is an illustrated cross-section of the human anatomy concerning the upper airway. Depicted in this figure is the Oropharynx 1, the Mouth 5, the Epiglottis 2, the Nasopharynx 4, the Esophagus 6, Tracheal Opening 7, and the Trachea 3. The esophagus is the structure which carries food downward, in to the stomach. It lies posterior to the Trachea. The function of the trachea is to provide a passageway for the exchange of gasses between the basic respiratory unit of the lung, the alveoli, and the atmosphere. The Trachea is the anatomical structure into which the endotracheal tube is to be placed using the described device.

The main purpose for the invention herein described, is to allow successful placement of the endotracheal tube under conditions which are described as constituting the difficult airway. As the practitioner becomes more skilled with the procedure, he or she may use this invention in cases where the airway anatomy is normal. It is important to stress that the advantage of this invention over others, and that which sets it apart from others, is the continued ventilation of the patient while fiberoptic laryngoscopy is carried out. Ventilation is only ceased when the introducer/stylette is already inserted into the trachea, and the endotracheal tube is prepared to advanced into place. The time of no ventilation should be no more than ten to twenty seconds.

The device may be used in the following way.

FIG. 1. The normal human anatomy is illustrated and comprises of the Mouth 5, the Oraphayrnx I, and the Trachea 3, via the Tracheal opening 7. The Esophagus 6 lies posterior to the Trachea, presenting the ever present hazard of the practitioner mistakenly placing the ventilating tube, the endotracheal tube, into the wrong anatomical structure, the Esophagus, instead of the proper anatomical structure, the Trachea.

FIG. 2. shows the Flexible Fiberoptic Laryngoscope/Bronchoscope, the FFLB, which consists of the light source 8, the body of the scope 9, the eyepiece 10, the controls 11 which move the flexible tip 13. Number 12 demonstrates the long flexible fiberoptic bundle of the scope.

Figure 3:
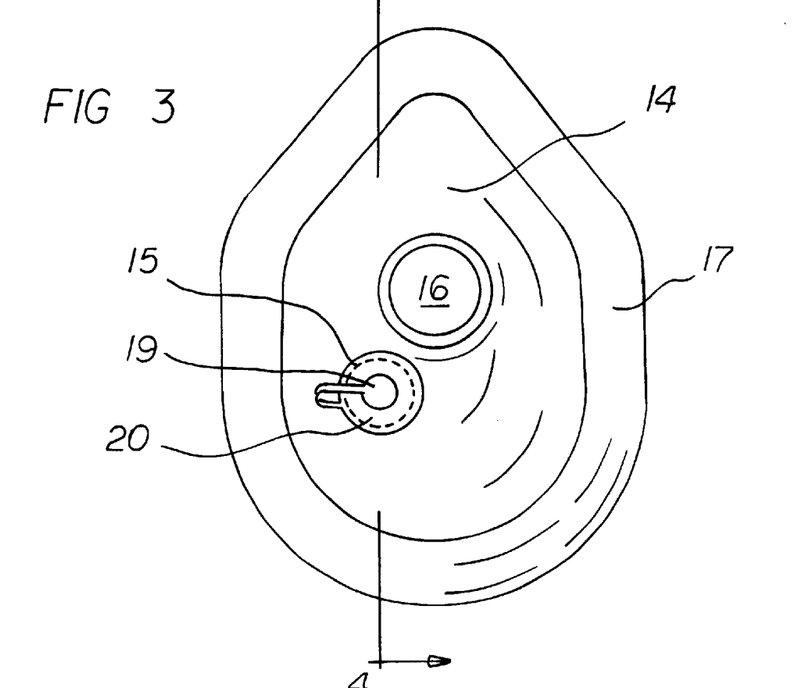
FIG. 3 is a superior view of the mask 14.

FIG. 3. shows the modified anesthesia mask, with it's soft air-filled face seal 17. The mask body 14, with its circuit connecting point 16 and FFLB access port 15 is demonstrated from this top view. The wall of the port 15 shows the relationship with the flexible distensible seal 20, which comes complete with a plug for the port 19, for those times when the port is not being utilized.

Figure 4:
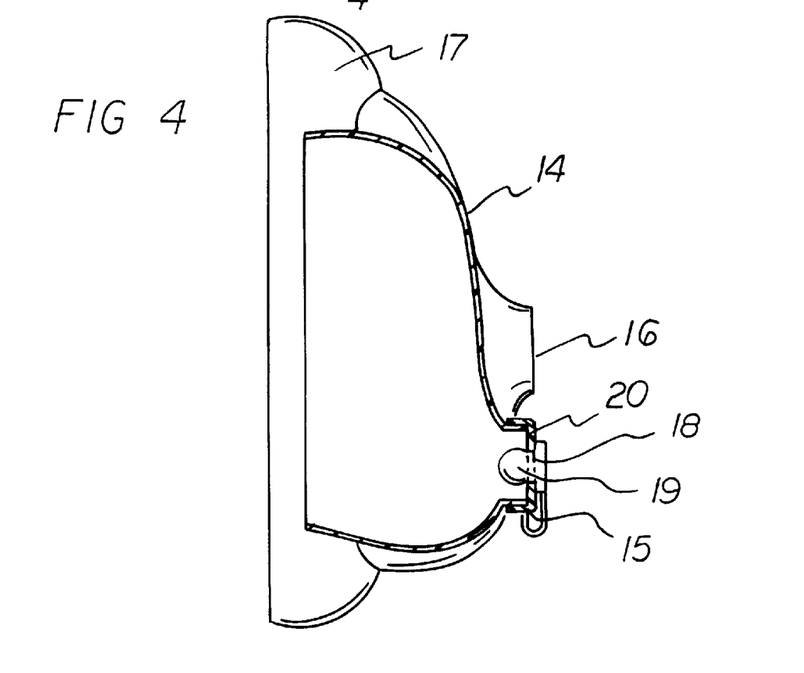
FIG. 4 is a cross section of the mask 14, taken along line 4—4 of FIG. 3.

FIG. 4. shows the cross section of the mask through the FFLB port. The firm wall of the mask 14 is again demonstrated. Plug 19 is in place in the FFLB distensible membrane 20. This figure demonstrates that there is a cross section through the midline of the port. The mask wall 14 is constructed of semi rigid material, preferably plastic. It has been cut showing the circuit connecting point 16 and the FFLB access port 15. The wall of the port 15, constructed of the same preferably semi-rigid material, shows the relationship with the flexible distensible seal 20, with the plug for the port 19, for those times when the port is not being utilized. The distensible seal 20 is made of a highly distensible material, like silastic, for accommodating the outside diameter of introducer/stylette. The port plug 19 may be constructed of a hard rubber-like material. The plug is blunt with a somewhat rounded distal end. At the proximal end of the obturator of the port, the plug outside diameter is lessened slightly. This lesser outside diameter allows the distensible port material to tighten on the plug, lessening the incidence of the port becoming unplugged when not in use.

Figure 5:
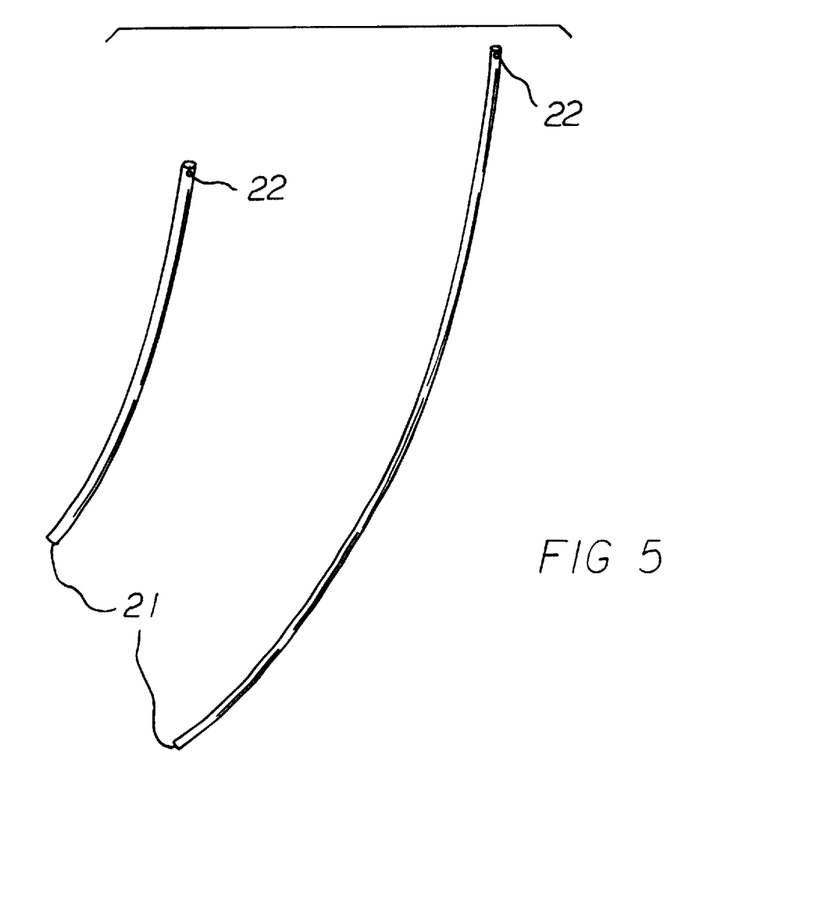
FIG. 5 is a view of the introducer/stylettes 27, depicting the difference in size, and the utilization of a threading aperture 22 in the shorter of the two intubating introducer/stylettes, with an enlarged view of the tip of the introducers, showing the rounded, beveled end.

FIG. 5. shows the intubating introducer/stylettes, which consist of a flexible semi rigid, plastic tube, approximately 30 centimeters in length and 70 centimeters in length. The inside diameter is large enough to accommodate the outside diameter of the FFLB, approximately 5 millimeters. The tip of the introducers are tapered and smooth 21 so as to avoid traumatizing the tissue of the trachea as it is passed over the FFLB into the trachea. On the opposite end of the shorter introducer/stylette, that end which would be outside the patient's airway, is an aperture 22 for allowing the thread to be placed through this end of the stylette/introducer. A large silk thread, approximately 40 inches in length is first passed through this aperture and knotted, so as to allow the thread passing through the aperture 22 to be loose. The silk is again knotted near the distal end. The looseness of the thread going through the aperture should be enough to allow the FFLB to be passes around it and down the introducer/stylette. The intubating introducer/stylettes are constructed of a semi rigid, plastic-like tube, the shorter introducer is approximately 35 centimeters in length and the longer is approximately 70 centimeters in length. The inside diameter is large enough to accommodate the outside diameter of the FFLB of approximately 5 millimeters. The tip of the introducers 21 are tapered, smooth, and diagonally cut so as to avoid traumatizing the tissue of the trachea as it is passed over the FFLB into the trachea. On the opposite end considered the distal end, that is, that end which would be outside the patient's airway, on the shorter of the two introducers, is a aperture 22 for allowing the thread to be easily placed through this end of the shorter, 35 cm., introducer/stylette. A large thread, such as silk, approximately 40 inches in length, is first passed through this aperture and knotted, so as to allow the thread passing through the aperture 22 to be loose. The thread is again knotted near the distal end. The looseness of the thread going through the hole should be enough to allow the FFLB to be passes around it and down the introducer/stylette.

Figure 6:
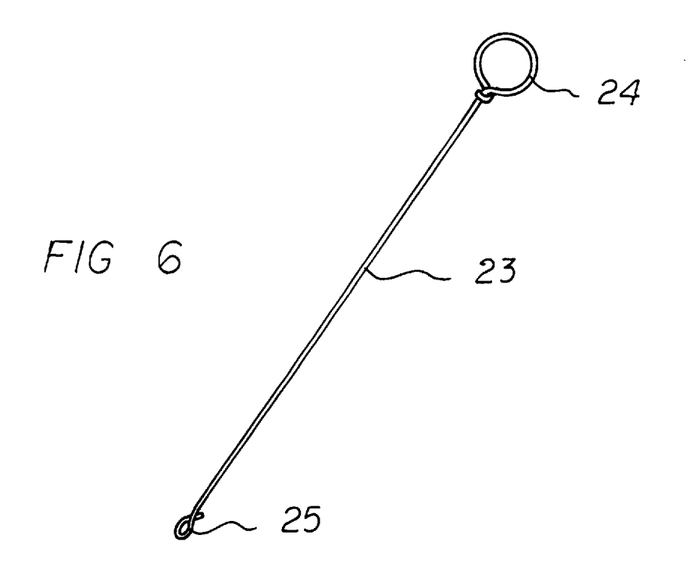
FIG. 6 is a view of the hook 23, demonstarting the finger hole 24 and the threading hook 25.

FIG. 6. shows the thread hook. This is a single length of wire, bent as demonstrated in the picture. On one end is a large loop, sized to accommodate a finger. On the other is a small hook, which has an overall diameter of less than 4 millimeters. This hook is approximately 20 inches long, allowing it to be placed through an endotracheal tube in preparation for the intubating procedure. The small hook 25 is passed through the endotracheal tube so that the small hook is protruding from the trachea side of the endotracheal tube. When this is done, the tube is placed aside, ready to be passed during the procedure. The thread hook is a single length of wire, made of a stiff wire-like material, bent as demonstrated in the drawing. This finger loop may be closed. This hook is open, allowing the thread to be ensnared easily.

Figure 7:
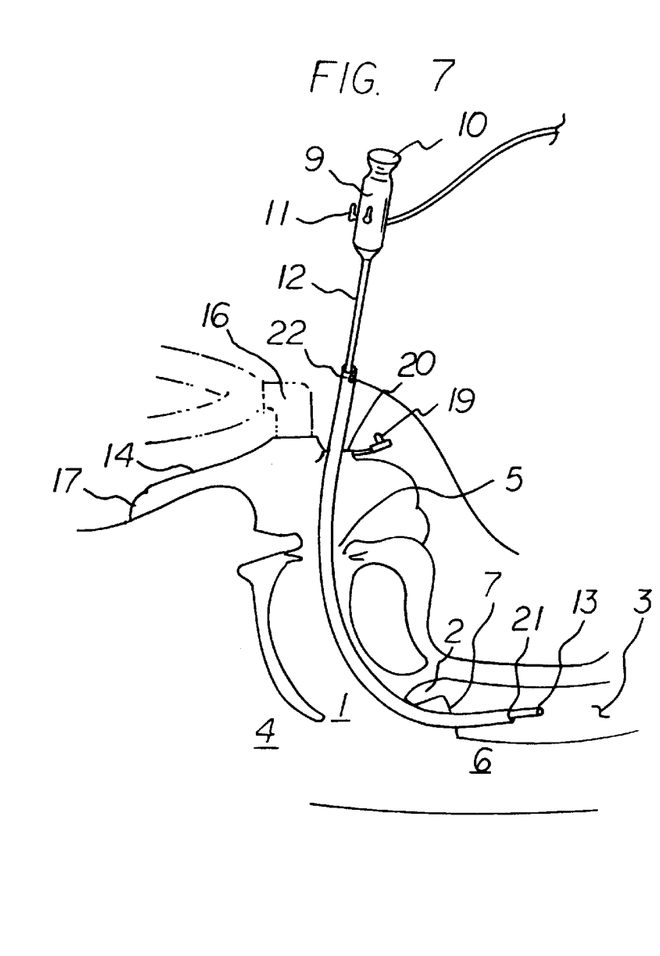
FIG. 7 is a cross sectional view along the midbody line of the anesthetized patient, depicting the employment of the fiberoptic scope and the shorter intubating introducer/stylette, through the mask port, into the mouth, and downward into the trachea.

FIG. 7. shows the intial procedure, after the hook has been placed through the endotracheal tube and set aside. The FFLB fiber bundle 12 has been threaded through the introducer and then advanced through the port, into the airway, and into the trachea. Once this has been accomplished, the introducer is advanced down the FFLB and into the airway, until it reaches the tip of the FFLB 13. This is ascertained by looking into the FFLB eyepiece 10 and seeing the view being covered by the stylette/introducer. Once this has been accomplished, the FFLB is removed, leaving the introducer in place in the airway. At this point the patient is still being ventilated via the mask. At this point, the mask is carefully slipped off the introducer. Ventilation stops at this time.

Figure 8:
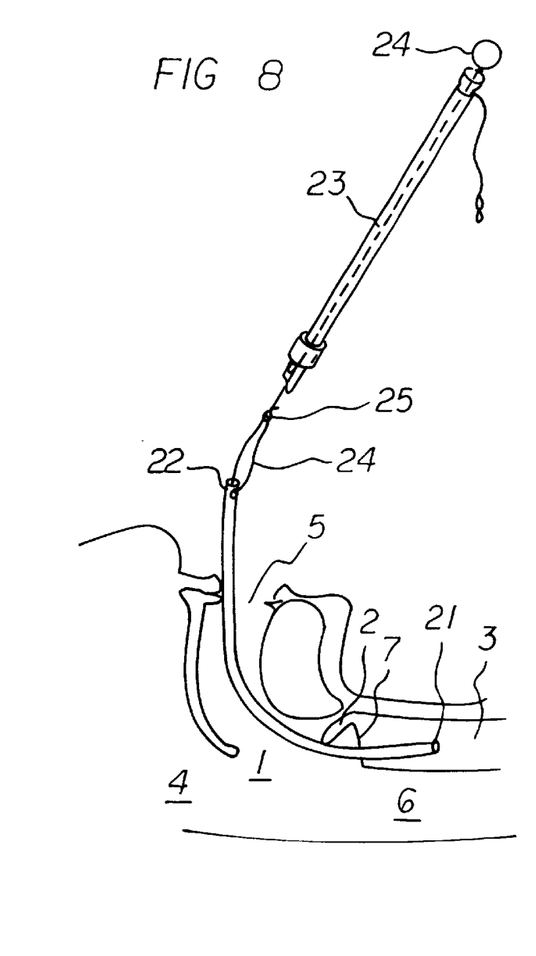
FIG. 8 is another cross section with the same orientation as FIG. 7 showing the mask has been removed, the fiberoptic scope has been removed, the introducer/stylette remains in the trachea, and the hook, which has been placed through the lumen of an endotracheal tube, captures the thread which holds the introducer/stylette via the thread aperture at the end.

FIG. 8. shows the hook, which had been previously placed through the endotracheal tube, hooking the thread 24 which is tied to the end of the introducer/stylette via the aperture 22. The hook is used to pull the silk thread 24 through the lumen of the endotracheal tube. The practitioner holds the thread as he or she advances the endotracheal tube down over the introducer/stylette to keep the introducer from migrating downward as the tube is advanced. The endotracheal tube may be rotated about the axis of the introducer to fascilitate passage when it enters the region of the tracheal opening.

Figure 9:
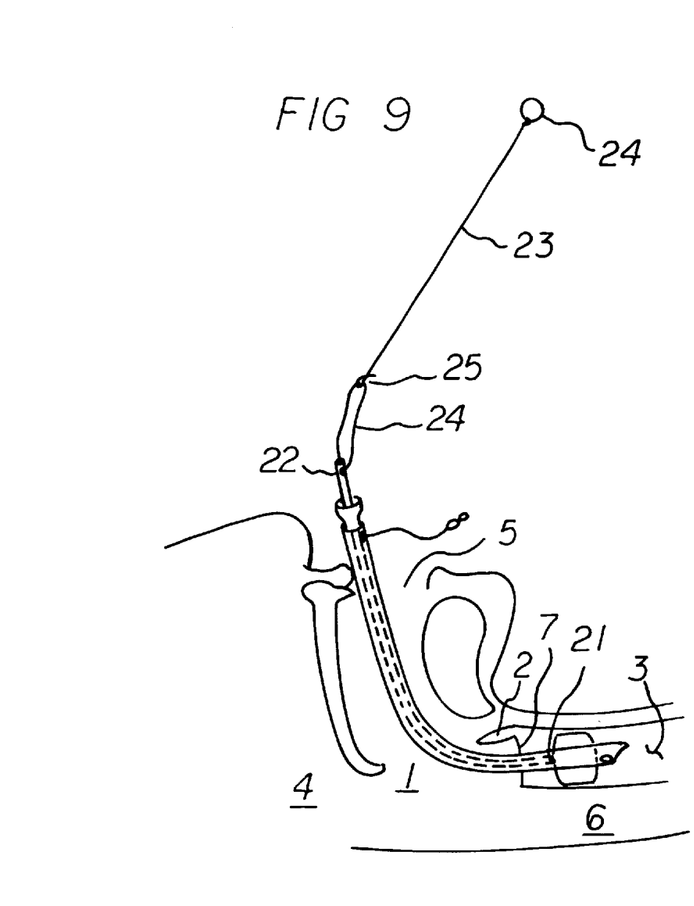
FIG. 9 is another orientation as set forth in FIG. 7 and FIG. 8, showing the hook pulling the thread, allowing the endotracheal tube to be advanced downward the airway, while the thread prevents the introducer/stylette from being advanced along with the tube, into the trachea.

FIG. 9. demonstrates the relationship of the endotracheal tube, hook, thread, and introducer with the patient's airway. Once the mask is removed, the practitioner quickly pulls the thread 24 through the lumen of the endotracheal tube, which aligns it on the introducer. Holding the thread, to keep the introducer from migrating as the tube is advanced, the endotracheal tube is slipped over the introducer and into the airway 3.

Figure 10:
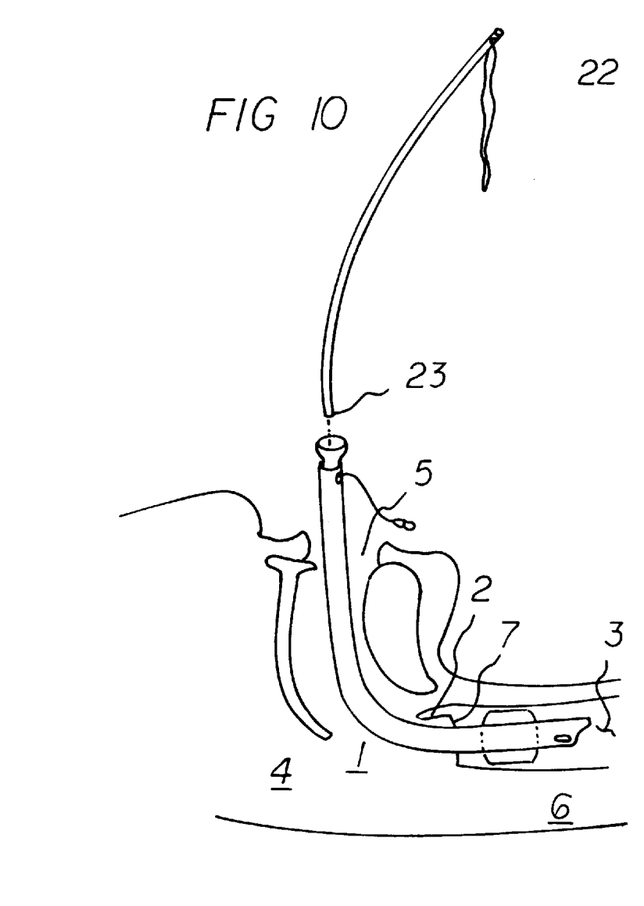
FIG. 10 is a view as set forth in FIGS. 7, 8 and 9 showing the removal of the introducer/stylette, leaving the endotracheal tube in place in the patient's trachea, the airway being sealed by the balloon at the end of the endotracheal tube.

FIG. 10. shows the endotracheal tube in the trachea and the introducer is being withdrawn from the lumen of the endotracheal tube. It is removed, leaving the endotracheal tube in the patient's airway 3. The distal tube balloon is inflated to seal the airway, and ventilation can resume, with the patient's airway secured.

Figure 11:
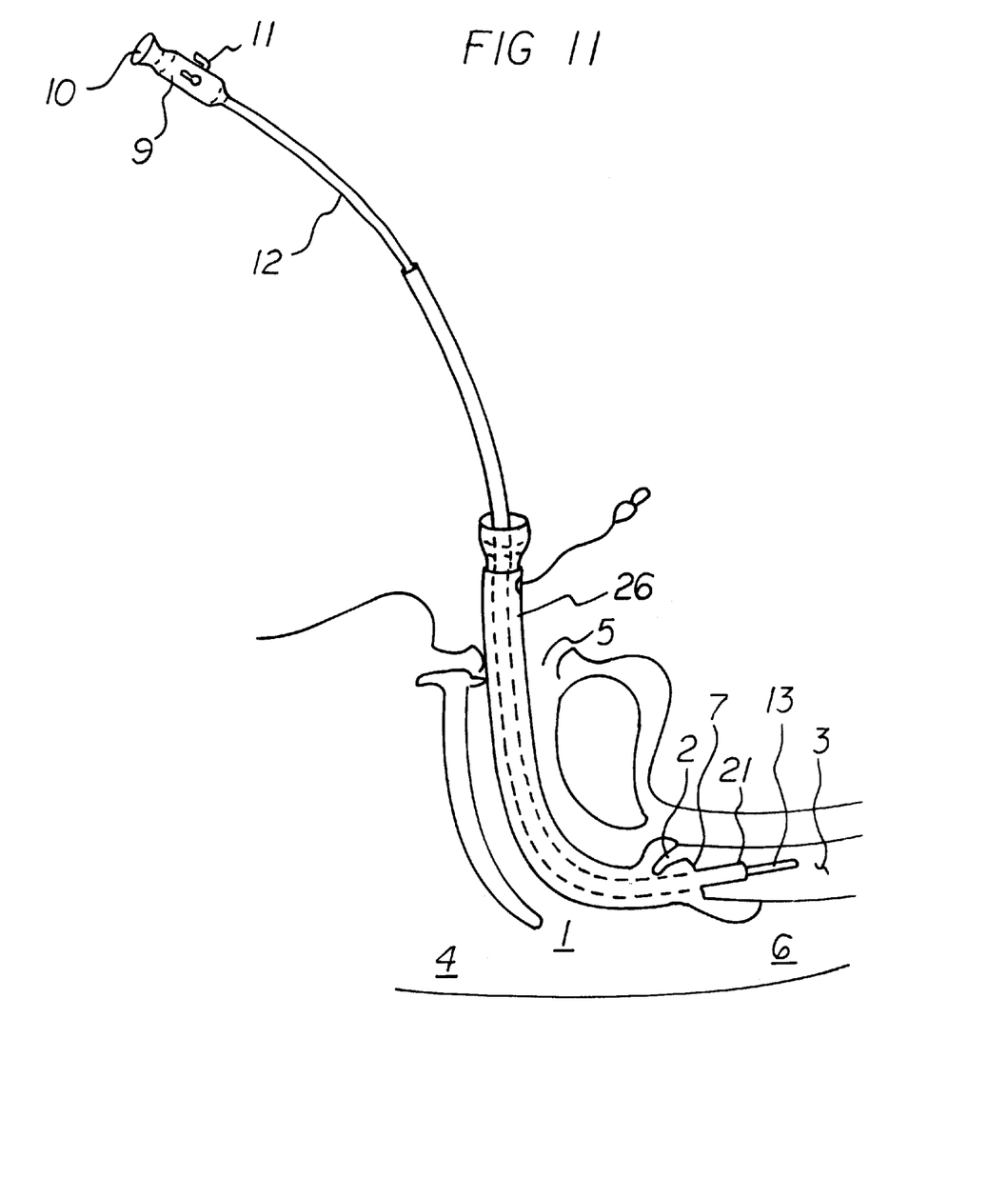
FIG. 11 is a view as set forth in FIGS. 7, 8, 9, and 10 showing the utilization of the longer intubating introducer/stylette, and fiberoptic scope 9 with the commonly used Laryngeal Mask Airway, (LMA) 26, demonstrating that the scope and introducer stylette may be advanced into the trachea via the lumen of the LMA.

FIG. 11. shows an LMA 26 in place with the long introducer being used along with a long fiberoptic device. A currently available ported connector is used between the gas circuit and the LMA. Once the introducer is in place, the fiberoptic will be removed as well as the LMA. An endotracheal tube will be slid over the introducer and into the trachea 3. Note that there is ample length of the introducer to allow control of the distal portion of the introducer as well as the proximal protion during the change over and before the endotracheal tube is advance into the patient's airway.

What is claimed is:

1. A device adapted for placement of an endotracheal tube into the trachea of an anesthetized patient while ventilating a patient, comprising:

an anesthesia mask having a pluggable port to be positioned over the mouth of a patient; and an elongated stylette/introducer having a proximal end for positioning into the trachea of a patient and a distal end located outside of the anesthesia mask adapted to be positioned over the mouth of a patient, the distal end having an aperture including a thread tied into the aperture to hold and to facilitate the advancement of an endotracheal tube over the elongated stylette/introducer into the airway of a patient without removing the anesthesia mask.

2. A method for placement of a stylette/introducer into the trachea of an anesthetized patient while ventilating, the method comprising the steps of;

placing an anesthesia mask having a pluggable port to be positioned over the mouth of a patient; and introducing into an elongated stylette/introducer device having a proximal end to be positioned into the trachea of a patient and a distal end located outside of the anesthesia mask to be positioned over the mouth of a patient, the distal end of the stylette/introducer having an aperture including a thread tied into the aperture to hold and to facilitate the advancement of an endotracheal tube over the elongated stylette/introducer into the airway of a patient without removing the anesthesia mask.

* * * * *